United States Patent
Vasilakos et al.

(10) Patent No.: US 10,583,134 B2
(45) Date of Patent: *Mar. 10, 2020

(54) METHODS AND THERAPEUTIC COMBINATIONS FOR TREATING TUMORS

(71) Applicants: 3M INNOVATIVE PROPERTIES COMPANY, St. Paul, MN (US); BOARD OF REGENTS, THE UNIVERSITY OF TEXAS SYSTEM, Austin, TX (US)

(72) Inventors: John Vasilakos, Woodbury, MN (US); Willem Overwijk, Houston, TX (US)

(73) Assignees: 3M INNOVATIVE PROPERTIES COMPANY, St. Paul, MN (US); BOARD OF REGENTS, THE UNIVERSITY OF TEXAS, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/964,604

(22) Filed: Apr. 27, 2018

(65) Prior Publication Data

US 2018/0243287 A1    Aug. 30, 2018

Related U.S. Application Data

(63) Continuation of application No. 15/500,618, filed as application No. PCT/US2015/043095 on Jul. 31, 2015, now Pat. No. 9,980,956.

(60) Provisional application No. 62/032,149, filed on Aug. 1, 2014.

(51) Int. Cl.
| | |
|---|---|
| *C07D 401/04* | (2006.01) |
| *A61K 31/4745* | (2006.01) |
| *A61K 39/395* | (2006.01) |
| *A61K 45/06* | (2006.01) |
| *A61P 35/00* | (2006.01) |
| *A61K 9/00* | (2006.01) |
| A61K 39/00 | (2006.01) |
| C07K 16/28 | (2006.01) |
| A61K 9/08 | (2006.01) |
| A61K 9/127 | (2006.01) |
| A61K 9/19 | (2006.01) |
| A61K 47/10 | (2017.01) |
| A61K 47/44 | (2017.01) |

(52) U.S. Cl.
CPC ........ *A61K 31/4745* (2013.01); *A61K 9/0019* (2013.01); *A61K 39/395* (2013.01); *A61K 45/06* (2013.01); *A61P 35/00* (2018.01); *A61K 9/08* (2013.01); *A61K 9/127* (2013.01); *A61K 9/19* (2013.01); *A61K 39/39558* (2013.01); *A61K 47/10* (2013.01); *A61K 47/44* (2013.01); *A61K 2039/505* (2013.01); *C07K 16/2818* (2013.01)

(58) Field of Classification Search
CPC ............ C07D 401/04; A61K 2039/505; A61K 31/4745
USPC ...................................... 514/314; 424/130.1
See application file for complete search history.

(56) References Cited

U.S. PATENT DOCUMENTS

| | | | |
|---|---|---|---|
| 9,980,956 B2 * | 5/2018 | Vasilakos | A61K 45/06 |
| 2004/0192585 A1 | 9/2004 | Owens et al. | |
| 2005/0171072 A1 | 8/2005 | Tomai et al. | |
| 2007/0123558 A1 | 5/2007 | Statham et al. | |
| 2008/0119508 A1 | 5/2008 | Slade et al. | |
| 2013/0018042 A1 | 1/2013 | Howbert et al. | |
| 2013/0230578 A1 | 9/2013 | Wightman | |
| 2016/0185870 A1 | 6/2016 | Van Eenennaam et al. | |
| 2017/0266280 A1 | 9/2017 | Rastelli et al. | |

FOREIGN PATENT DOCUMENTS

| | | |
|---|---|---|
| WO | WO 2007113648 A2 | 10/2007 |
| WO | WO 2012024284 | 2/2012 |
| WO | WO 2013173223 | 11/2013 |
| WO | WO 2014/201245 A1 | 12/2014 |

OTHER PUBLICATIONS

Smirnov et al, 'Intratumoral immunotherapy with the TLR7/8 agonist 3M-052', Journal for ImmunoTherapy of Cancer 2013, 1, (Suppl 1):P138, p. 1.
Extended European Search Report related to European Application No. 15827277.3, dated Jan. 18, 2018.
Sing, M., et al., "Effective Innate and Adaptive Antimelanoma Immunity through Localized TLR7/8 Activation," The Journal of Immunology, vol. 193, No. 9, Sep. 24, 2014, pp. 4722-4731.

* cited by examiner

*Primary Examiner* — Raymond J Henley, III
(74) *Attorney, Agent, or Firm* — Eric E. Silverman

(57) ABSTRACT

Methods and therapeutic combinations useful for increasing cell-mediated anti-tumor responses are described. The methods include administering to a subject a therapeutically effective amount of an Immune Response Modifier Compound and a therapeutically effective amount of one or more immune checkpoint inhibitor compounds.

5 Claims, 3 Drawing Sheets

METHODS AND THERAPEUTIC COMBINATIONS FOR TREATING TUMORS

CROSS-REFERENCE TO RELATED APPLICATIONS

This application is a continuation of U.S. application Ser. No. 15/500,618, filed Jul. 31, 2015 and issued as U.S. Pat. No. 9,980,956, said U.S. application Ser. No. 15/500,618, is a U.S. National Stage application of International Application No. PCT/US2015/043095, filed on Jul. 31, 2015, said International Application No. PCT/US2015/043095 claims benefit under 35 U.S.C. § 119(e) of the U.S. Provisional Application No. 62/032,149, filed Aug. 1, 2014. Each of the above listed applications is incorporated by reference herein in its entirety for all purpose.

This invention was made with government support under grant numbers CA143077 and CA093459 awarded by the National Institutes of Health. The government has certain rights in the invention.

BACKGROUND

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

They may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H2$-mediated diseases (e.g., asthma, allergic rhinitis, atopic dermatitis), auto-immune diseases (e.g., multiple sclerosis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929; and International Publication Number WO 2005/079195) and more are still being discovered. Other IRMs have higher molecular weights, such as oligonucleotides, including CpGs (see, e.g., U.S. Pat. No. 6,194,388).

In view of the great therapeutic potential for IRMs, and despite the important work that has already been done, there is a substantial ongoing need to expand their uses and therapeutic benefits. In particular, there is a need to investigate new methods and therapeutic combinations that enhance anti-tumor immune responses and outcomes.

SUMMARY

Responses of the immune system to threats such as tumors are modulated or controlled by highly complex immune activation and deactivation signaling pathways. The entirety of how signaling pathways and compensatory feedback mechanisms interact to influence an anti-tumor immune response is only partially understood and thus presents the opportunity for identifying new therapeutic combinations and methods.

IRM compounds work through TLR pathways of the immune system to activate multiple cell-mediated anti-tumor immune responses (such as for example T-cell activation). It is known that the immune system naturally utilizes a family of what are known as checkpoint receptors as a compensatory means to downregulate activated immune cells such as T-cells in order to protect against autoimmunity. Many tumors have developed methods to evade an anti-tumor immune response in the tumor environment by expressing agonistic surface proteins to checkpoint receptors. A method involving the combination of immune activation with an IRM compound and blockade of immune checkpoint pathways with immune checkpoint inhibitor compounds should help to maintain and enhance IRM initiated anti-tumor immune responses.

It has been found that administration of the IRM compound N-(4-{[4-amino-2-butyl-1H-imidazo[4,5-c]quinolin-1-yl]oxy}butyl)octadecanamide [compound of formula (I)] in combination with at least one immune checkpoint inhibitor compound enhances the immune response to a tumor. It has further been found that the combination of the IRM compound of formula (I) with at least one immune checkpoint inhibitor compound may result in a surprising improvement in anti-tumor response as evidenced by a significantly reduced rate in tumor growth as compared to individual treatment with the IRM compound of formula (I) or immune checkpoint inhibitor compounds used alone (i.e., not in combination).

It has also surprisingly been found that when using a method where one or more immune checkpoint inhibitor compounds are administered systemically (intraperitoneal) and the compound of formula (I) is administered in a way so that it is primarily localized and maintained at a tumor site (intratumoral injection), the growth of tumors distant from the intratumoral injection site may also be inhibited. This result occurs even at dose concentrations of the immune checkpoint inhibitor compounds where systemic administration of only the immune checkpoint inhibitor compounds (without administration of the compound of formula (I)) has been shown to be largely ineffective.

Accordingly, in one aspect, the present disclosure provides a method for treating a subject having a tumor comprising administration of a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another aspect, the present disclosure provides a method of inhibiting the growth of tumor cells in a subject comprising administration of a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (T)) or a pharmaceutically acceptable salt thereof.

In another aspect, the present disclosure provides a method for increasing a cell-mediated immune response of a cell population that includes cells of a tumor, the method comprising administering a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another aspect, the present disclosure provides for a therapeutic combination for treating a tumor comprising a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another aspect, the present disclosure provides for a therapeutic combination for increasing a cell-mediated immune response of a cell population comprising a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

For the sake of convenience as used herein the terms "N-(4-{[4-amino-2-butyl-1H-imidazo[4,5-c]quinolin-1-yl]oxy}butyl)octadecanamide" and "compound of formula (I)", and "IRM compound of formula (I)" are used interchangeably.

N-(4-{[4-amino-2-butyl-1H-imidazo[4,5-c]quinolin-1-yl]oxy}butyl)octadecanamide [compound of formula (I)]:

"Ameliorate" refers to any reduction in the extent, severity, frequency, and/or likelihood of a symptom or clinical sign characteristic of a particular condition.

"Antibody fragment" refers to a sub-portion of an antibody that retains at least some of the binding function of the parent antibody toward a ligand.

"Antibody derivative" refers to a chemically modified version of an antibody or antibody fragment. Some examples of derivatives include attachment to other functional molecules such a PEG groups, peptides, proteins or other antibodies.

"Block", "blocking", "blockade" and variations thereof have the same meaning as "inhibit", "inhibiting", "inhibition" and variations thereof. The term "blockade" is meant to encompass both partial and complete blockade.

"Cell-mediated immune activity" refers to a biological activity considered part of a cell-mediated immune response such as, for example, an increase in the production of at least one $T_H1$ cytokine.

"Human antibody" refers to antibodies with variable and constant regions identical to, essentially identical to, or derived from human germline immunoglobulin sequences.

Compound of formula (I)

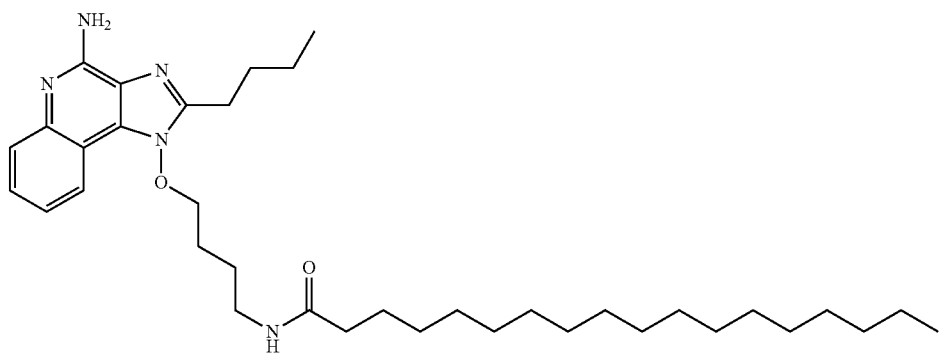

As used herein, "a", "an", "the", "at least one", and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

"Agonist" refers to a compound that can combine with a receptor (e.g., a TLR) to induce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound binds to the receptor. With regard to TLRs, an agonist may be referred to as an agonist of a particular TLR or a particular combination of TLRs (e.g., a TLR 7/8 agonist—being an agonist of both TLR7 and TLR8).

"Antagonist" refers to a compound that can combine with a receptor (e.g., an immune checkpoint receptor) to block a cellular activity. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the receptor.

Human antibodies can include amino acid sequences generated from random or site specific mutations. As used herein, the term human antibodies includes human antibody derivatives.

"Immune cell" refers to cell of the immune system, i.e., a cell directly or indirectly involved in the generation or maintenance of an immune response, whether the immune response is innate, acquired, humoral, or cell-mediated.

"Humanized antibody" refers to antibodies with CDR sequences from a non-human mammalian species grafted onto a human immunoglobulin framework. As used herein, the term humanized antibodies includes humanized antibody derivatives.

"Immune checkpoint inhibitor compound" refers to a molecule (e.g., small molecule, peptide, polypeptide, protein, antibody, antibody fragment and the like) that acts as an inhibitor (antagonist) of an immune checkpoint pathway. Inhibition of a pathway can include blockade of the pathway through binding to a receptor or signaling molecule that is part of the immune checkpoint pathway.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Liposome" refers generally to a self-assembling particle composed of amphipathic molecules such as, but not limited to lipid, lipid-like, or polymeric substances. Liposomes can also include lipopeptides, glycolipids, cholesterol and combinations thereof. Liposomes also can include one or more groups that selectively target delivery to certain cells or tissues.

"Pharmaceutically acceptable formulations" can deliver therapeutically effective amounts of the compounds of the disclosure to a subject by a chosen route of administration, are generally tolerated by the subject, and have an acceptable toxicity profile (preferably minimal to no toxicity at an administered dose). Suitable pharmaceutically acceptable formulations are described in Remington's Pharmaceutical Sciences, 18$^{th}$ Edition (1990), Mack Publishing Co. and can be readily selected by one of ordinary skill in the art.

"Pharmaceutically acceptable salt" refers to a derivative of a compound in which the compound is modified by converting at least one acid or base group in the compound to a non-toxic salt form. Examples of "pharmaceutically acceptable salts are described by Berge in *Journal of Pharmaceutical Science* (1977), 66, pages 1-19, and include acid addition salts and base addition salts. Acid addition salts include mineral or organic acid salts of basic moieties in a compound (such as amine groups). Suitable acid addition salts include those derived from inorganic acids such as for example hydrochloric acid, hydrobromic acid, sulfuric acid, nitric acid, and the like. Suitable acid addition salts derived from organic acids such as mono- and di-carboxylic acids (e.g., acetic acid, propionic acid), hydroxyalkonic acids (e.g., citric acid, tartaric acid), aromatic acids (e.g., benzoic acid, xinofoic acid, pamoic acid), aliphatic and aromatic sulfonic acids (e.g., para-toluene sulfonic acid), and the like. Base addition salts include alkaline earth mineral salts and organic amine salts of acidic moieties in a compound (such as carboxylic acid groups). Suitable base addition salts include sodium, potassium, magnesium, calcium salts, and the like. Additional suitable base addition salts include non-toxic organic amines such as choline, ethylenediamine, and the like.

"Preferred" and "Preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Sign" or "clinical sign" refers to an objective physical finding relating to a particular condition capable of being found by one other than the subject.

"Subject" or "Patient" as used herein are synonymous and refer to a human adult, child, or infant.

"Symptom" refers to any subjective evidence of disease or of a subject's condition.

"Therapeutic" and variations thereof refer to a treatment that ameliorates one or more existing symptoms or clinical signs associated with a condition.

"Treat" and variations thereof refer to reducing, limiting progression, ameliorating, preventing, or resolving, to any extent, the symptoms or signs related to a condition.

It is to be understood that the phraseology and terminology as used herein is for the purpose of description and should not be regarded as limiting. The use of the terms "includes", "comprises", "has" or "have" and variations thereof herein is meant to encompass the items listed thereafter and equivalents thereof as well as additional items.

The above summary of the present disclosure is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION

Figure 1:
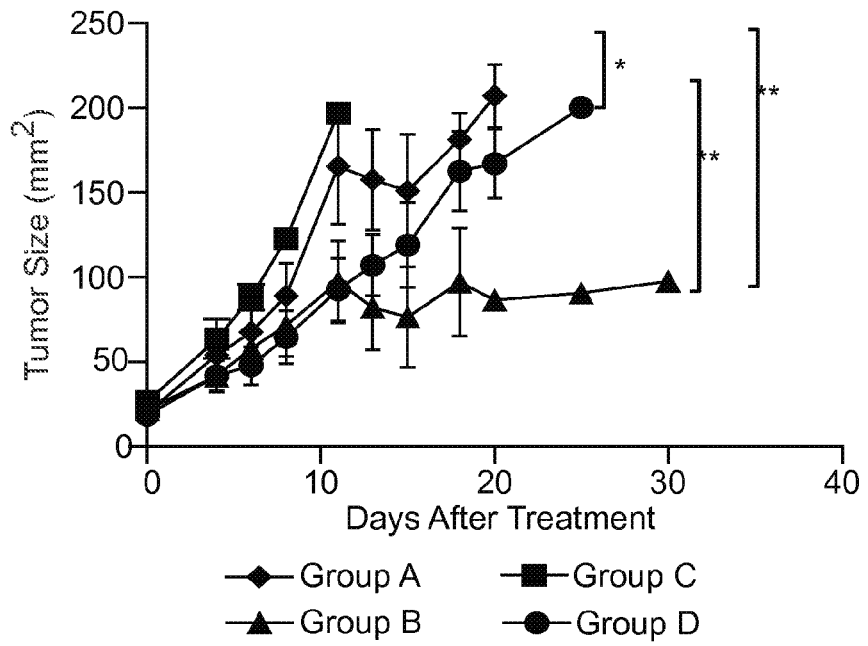
FIG. 1 is a chart of the growth in tumor size over time and compares treatment with a therapeutic combination of the compound of formula (I)+anti-CTLA-4 antibody (Group B) to monotherapy and vehicle control groups (Groups A, C, and D).

The present disclosure provides methods and therapeutic compositions for treating a tumor comprising administration of a therapeutically effective amount of the IRM compound N-(4-{[4-amino-2-butyl-1H-imidazo[4,5-c]quinolin-1-yl]oxy}butyl)octadecanamide [compound of formula (I)] and a therapeutically effective amount of one or more immune checkpoint inhibitor compounds. The compound of formula (I) activates the immune response at a tumor site by activation of toll-like receptor 7 (TLR7) and toll-like receptor 8 (TLR8) signaling pathways. As such the compound of formula (I) is referred to as a TLR 7/8 agonist. Anti-tumor immune responses activated by the compound of formula (I) include, but are not limited to, increased levels of interferon-alpha; interferon-gamma; interferon inducible proteins; TNF-alpha, chemokines such as CCL2, CCL3, CCL4, CXCL2; activated T-cells; activated B-cells; tumor specific T-cells; activated tumor associated macrophages; chemokine receptors such as CCR6; and tumor-associated lymphoid aggregates.

Immune checkpoint inhibitor compounds act by blocking inhibitory immune checkpoint pathways that downregulate or inhibit one or more of the following: activation of T-cell cells; activation of antigen presenting cells (such as dendritic cells, B-cells, and macrophages); innate immune cells that have anticancer activity such as NK cells. A treatment regimen combining the IRM compound of formula (I) with an immune checkpoint inhibitor compound increases the anti-tumor immune response through complementary upregulation of immune pathways that enhance or activate the anti-tumor immune response (with the IRM compound of formula (I)) and blocking (or inhibiting) pathways that downregulate the anti-tumor immune response (with immune checkpoint inhibitor compounds).

It is believed that the combination therapy of the disclosure can be especially beneficial when there is a weak (ineffective) endogenous anti-tumor immune response to the tumor by the subject. The beneficial effect of the IRM compound of formula (I) is that it can convert the weak endogenous anti-tumor immune response to a strong response through activation of both innate (e.g., IFN-alpha and IL-12 production) and humoral (e.g., tumor specific T-cell production) pathways. However, it is believed that immune response activation by the IRM compound of formula (I) can also cause a subsequent compensatory (and undesired) downregulation of the immune response in the tumor environment by the activation of one or more immune checkpoint pathways. As an example, compensatory activation of an immune checkpoint pathway can result in increased checkpoint ligand expansion on tumor cells and/or tumor-associated macrophages (TAMS) which lead to increased signaling for downregulation of the immunologic anti-tumor response. Administration of at least one checkpoint inhibitor compound can block these checkpoint pathways so that the enhanced anti-tumor immune response from administration of the IRM compound of formula (I) can be maintained, extended in duration, and in some cases enhanced. In a situation where there is a weak (ineffective) endogenous anti-tumor immune response to a tumor by the subject, treatment involving only the administration of one or more checkpoint inhibitor compounds (i.e., the compound of formula (I) is not administered) may not be sufficient to generate an effective anti-tumor response.

N-(4-{[4-amino-2-butyl-1H-imidazo[4,5-c]quinolin-1-yl]oxy}butyl)octadecanamide [compound of formula (I)] has the following structure:

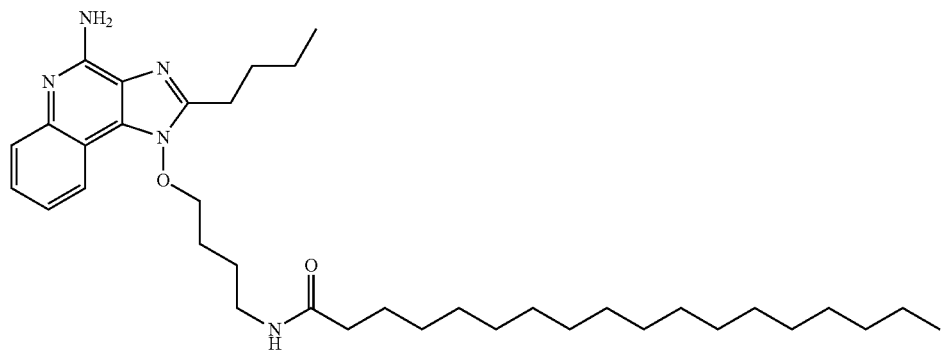 [SMILES: CCCCCCCCCCCCCCCCCC(=O)NCCCCOn1c(CCCC)nc2c(N)nc3ccccc3c21]

In one embodiment, the present disclosure provides a method for treating a subject having a tumor comprising administration of a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (T)) or a pharmaceutically acceptable salt thereof.

In one embodiment, the present disclosure provides a method of inhibiting the growth of tumor cells in a subject comprising administration of a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another embodiment, the present disclosure provides a method for increasing a cell-mediated immune response of a cell population that includes cells of a tumor, the method comprising administering a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another embodiment, the present disclosure provides for a therapeutic combination for treating a tumor comprising a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In another embodiment, the present disclosure provides for a therapeutic combination for increasing a cell-mediated immune response of a cell population comprising a therapeutically effective amount of one or more immune checkpoint inhibitor compounds and a therapeutically effective amount of the IRM compound N-(4-{[4-amino-2-butyl-1H-imidazo[4,5-c]quinolin-1-yl]oxy}butyl)octadecanamide (compound of formula (I)) or a pharmaceutically acceptable salt thereof.

In one embodiment of the present disclosure, the compound of formula (I) is incorporated in a pharmaceutically acceptable formulation. In some embodiments, the compound of formula (I) is incorporated in an injectable formulation. In some embodiments the compound of formula (I) is incorporated in an injectable formulation that substantially maintains the compound of formula (I) at or near the injection site.

In some embodiments of the present disclosure, the compound of formula (I) is incorporated in a formulation comprising vegetable oil. In some embodiments the vegetable oil is selected from sesame oil, canola oil, castor oil, coconut oil, corn oil, olive oil, palm oil, safflower oil, soybean oil, sunflower oil, or peanut oil.

In some embodiments the compound of formula (I) is incorporated in a formulation comprising sesame oil. In some embodiments the compound of formula (I) is incorporated in a formulation comprising sesame oil and ethanol. The amount of ethanol in a formulation is reported as the weight percent (wt-%) of ethanol in the formulation. In some embodiments the compound of formula (I) is incorporated in a formulation comprising sesame oil and ethanol from 1 wt-% to 9 wt-%. In some embodiments the compound of formula (I) is incorporated in a formulation comprising sesame oil and ethanol from 7 wt-% to 8 wt-%. In some embodiments the sesame oil used in the formulations described herein is pharmaceutical grade, such as Sesame Oil, NF. In some embodiments, the sesame oil may be refined such that one or more polar compounds have been substantially removed from the sesame oil or reduced in content without substantially altering the fatty acid profile of the sesame oil. Further information on such formulations may be found in U.S. Patent Application Ser. No. 61/900,255 filed Nov. 5, 2013.

In some embodiments of the present disclosure, the compound of formula (I) is incorporated in an ethanol formulation. In some embodiments, the ethanol does not contain any water or denaturant. Exemplary ethanol useful in the formulations of the present disclosure includes 200 proof ethanol, e.g., Dehydrated Alcohol, USP grade.

In some embodiments of the present disclosure, the compound of formula (I) is incorporated in a pharmaceutically acceptable liposome formulation. One example of a pharmaceutically acceptable liposome formulation of the compound of formula (I) using dioleoylphosphatidylcholine (DOPC) is described in Example 2 of U.S. Patent Application No. 2013/0230578 (Wightman).

In some embodiments of the present disclosure, the compound of formula (I) is incorporated in a pharmaceutically acceptable formulation and the pharmaceutically acceptable formulation is administered by intradermal, subcutaneous, or intramuscular injection.

In some embodiments of the present disclosure, the compound of formula (I) is incorporated in a pharmaceutically acceptable formulation and the pharmaceutically acceptable formulation is injected directly into a tumor (i.e., intratumoral injection). In some embodiments, the compound of formula (I) is incorporated in a pharmaceutically acceptable formulation and the pharmaceutically acceptable formulation is injected into the peritumoral region surrounding a tumor. The peritumoral region can contain antitumor immune cells.

It is expected that on injection the compound of formula (T) is generally localized and maintained at the injection site for an extended period of time. As such, the compound of formula (I) may induce cytokine production at the site of administration (or at a local site of application) and may do so without substantial systemic cytokine induction (for example TNF-alpha).

Additional pharmaceutical formulations suitable for administration of the compound of formula (I) include, but are not limited to, solution, suspension and emulsion formulations. Types of formulations include, but are not limited to aqueous formulations (e.g., phosphate or citrate buffered saline), oil formulations, polyol formulations (e.g., glycerol, polyethylene glycol), oil in water formulations, and water in oil formulations. Pharmaceutical formulations may further include one or more additives such as suspending agents, colorants, surfactants, and dispersing agents.

A review describing immune checkpoint pathways and the blockade of such pathways with immune checkpoint inhibitor compounds is provided by Pardoll in *Nature Reviews Cancer* (April, 2012), pages 252-264. Immune check point inhibitor compounds display anti-tumor activity by blocking one or more of the endogenous immune checkpoint pathways that downregulate an anti-tumor immune response. The inhibition or blockade of an immune checkpoint pathway typically involves inhibiting a checkpoint receptor and ligand interaction with an immune checkpoint inhibitor compound to reduce or eliminate the down regulation signal and resulting diminishment of the anti-tumor response.

In some embodiments of the present disclosure, the immune checkpoint inhibitor compound inhibits the signaling interaction between an immune checkpoint receptor and the corresponding ligand of the immune checkpoint receptor. The immune checkpoint inhibitor compound can act by blocking activation of the immune checkpoint pathway by inhibition (anatagonism) of an immune checkpoint receptor (some examples of receptors include CTLA-4, PD-1, LAG-3, TIM-3, BTLA, and KIR) or by inhibition of a ligand of an immune checkpoint receptor (some examples of ligands include PD-L1 and PD-L2). In such embodiments, the affect of the immune checkpoint inhibitor compound is to reduce or eliminate down regulation of certain aspects of the immune system anti-tumor response in the tumor microenvironment.

The immune checkpoint receptor cytotoxic T-lymphocyte associated antigen 4 (CTLA-4) is expressed on T-cells and is involved in signaling pathways that reduce the level of T-cell activation. It is believed that CTLA-4 can downregulate T-cell activation through competitive binding and sequestration of CD80 and CD86. In addition, CTLA-4 has been shown to be involved in enhancing the immunosuppressive activity of $T_{Reg}$ cells.

The immune checkpoint receptor programmed death 1 (PD-1) is expressed by activated T-cells upon extended exposure to antigen. Engagement of PD-1 with its known binding ligands, PD-L1 and PD-L2, occurs primarily within the tumor microenvironment and results in downregulation of anti-tumor specific T-cell responses. Both PD-L1 and PD-L2 are known to be expressed on tumor cells. The expression of PD-L1 and PD-L2 on tumors has been correlated with decreased survival outcomes.

The immune checkpoint receptor lymphocyte activation gene 3 (LAG-3) is expressed on anergic T-cells and T-reg cells. LAG-3 is involved in signaling pathways that send inhibitory message to activated effector T-cells. LAG-3 also upregulates immunosuppressive $T_{Reg}$ cell activity.

The immune checkpoint receptor T cell membrane protein 3 (TIM-3) is expressed on Th1 and Tc1 cells, but not other T-cells. Interaction of TIM-3 with its ligand, gallectin-9, produces a Th1 cell death signal. TIM-3 has been reported to play a role in maintaining T-cell exhaustion and blockade of TIM-3 has been shown to restore activity to exhausted T-cells.

The immune checkpoint receptor B- and T-lymphocyte attenuator (BTLA) receptor is expressed on both resting and activated B-cells and T-cells. Activation of BTLA when combined with its ligand HVEM (herpes virus entry mediator) results in downregulation of both T-cell activation and proliferation. HVEM is expressed by certain tumors (e.g., melanoma) and tumor-associated endothelial cells.

The immune checkpoint receptors known as killer cell immunoglobulin-like receptors (KIR) are a polymorphic family of receptors expressed on NK cells and some T-cells and function as regulators of immune tolerance associated with natural killer (NK) cells. Blocking certain KIR receptors with inhibitor compounds can facilitate the destruction of tumors through the increased activity of NK cells.

In some embodiments of the present disclosure, the immune checkpoint inhibitor compound is a small organic molecule (molecular weight less than 1000 daltons), a peptide, a polypeptide, a protein, an antibody, an antibody fragment, or an antibody derivative. In some embodiments, the immune checkpoint inhibitor compound is an antibody. In some embodiments, the antibody is a monoclonal antibody, specifically a human or a humanized monoclonal antibody.

Monoclonal antibodies, antibody fragments, and antibody derivatives for blocking immune checkpoint pathways can be prepared by any of several methods known to those of ordinary skill in the art, including but not limited to, somatic cell hybridization techniques and hybridoma, methods. Hybridoma generation is described in *Antibodies, A Laboratory Manual, Harlow and Lane,* 1988, Cold Spring Harbor Publications, New York. Human monoclonal antibodies can be identified and isolated by screening phage display libraries of human immunoglobulin genes by methods described for example in U.S. Pat. Nos. 5,223,409, 5,403,484, 5,571,698, 6,582,915, and 6,593,081. Monoclonal antibodies can be prepared using the general methods described in U.S. Pat. No. 6,331,415 (Cabilly).

As an example, human monoclonal antibodies can be prepared using a XenoMouse™ (Abgenix, Freemont, Calif.) or hybridomas of B cells from a XenoMouse. A XenoMouse is a murine host having functional human immunoglobulin genes as described in U.S. Pat. No. 6,162,963 (Kucherlapati).

Methods for the preparation and us of immune checkpoint antibodies are described in the following illustrative publications. The preparation and therapeutic uses of anti-CTLA-4 antibodies are described in U.S. Pat. No. 7,229,628 (Allison), U.S. Pat. No. 7,311,910 (Linsley), and U.S. Pat. No. 8,017,144 (Korman). The preparation and therapeutic uses of anti-PD-1 antibodies are described in U.S. Pat. No. 8,008,449 (Korman) and U.S. Patent Application No. 2011/0271358 (Freeman). The preparation and therapeutic uses of anti-PD-L1 antibodies are described in U.S. Pat. No. 7,943,743 (Korman). The preparation and therapeutic uses of anti-TIM-3 antibodies are described in U.S. Pat. No. 8,101,176 (Kuchroo) and U.S. Pat. No. 8,552,156 (Tagayanagi). The preparation and therapeutic uses of anti-LAG-3 antibodies are described in U.S. Patent Application No. 2011/0150892 (Thudium) and International Publication Number WO2014/008218 (Lonberg). The preparation and therapeutic uses of anti-KIR antibodies are described in U.S. Pat. No. 8,119,775 (Moretta). The preparation of antibodies that block BTLA regulated inhibitory pathways (anti-BTLA antibodies) are described in U.S. Pat. No. 8,563,694 (Mataraza).

In some embodiments of the present disclosure, the immune checkpoint inhibitor compound is a CTLA-4 receptor inhibitor, a PD-1 receptor inhibitor, a LAG-3 receptor inhibitor, a TIM-3 receptor inhibitor, a BTLA receptor inhibitor, or a KIR receptor inhibitor. In some embodiments, the immune checkpoint inhibitor compound is an inhibitor of PD-L1 or an inhibitor of PD-L2.

In some embodiments of the present disclosure, the immune checkpoint inhibitor compound is an inhibitor of the PD-L1/PD-1 pathway or the PD-L2/PD-1 pathway. In some embodiments, the inhibitor of the PD-L1/PD-1 pathway is MEDI4736.

In some embodiments of the present disclosure, the immune checkpoint inhibitor compound is an anti-CTLA-4 receptor antibody, an anti-PD-1 receptor antibody, an anti-LAG-3 receptor antibody, an anti-TIM-3 receptor antibody, an anti-BTLA receptor antibody, an anti-KIR receptor antibody, an anti-PD-L1 antibody, or an anti-PD-L2 antibody.

In some embodiments of the present disclosure, the method comprises administering the IRM compound of formula (I) and an immune checkpoint inhibitor compound.

In some embodiments, the method comprises treating a subject having a tumor by administering therapeutically effective amounts of the IRM compound of formula (I) and a CTLA-4 receptor inhibitor compound. In some embodiments, the method comprises treating a subject having a tumor by administering therapeutically effective amounts of the IRM compound of formula (I) and a PD-1 receptor inhibitor compound.

In some embodiments of the present disclosure, the method comprises treating a subject having a tumor by administering therapeutically effective amounts of the IRM compound of formula (I) and a LAG-3 receptor inhibitor compound. In some embodiments, the method comprises treating a subject having a tumor by administering therapeutically effective amounts of the IRM compound of formula (I) and a TIM-3 receptor inhibitor compound. In some embodiments, the method comprise treating a subject having a tumor by administering therapeutically effective amounts of the IRM compound of formula (I) and a BTLA receptor inhibitor compound. In some embodiments, the method comprises treating a subject having a tumor by administering therapeutically effective amounts of the IRM compound of formula (I) and a KIR receptor inhibitor compound. In some embodiments, the method comprises treating a subject having a tumor by administering therapeutically effective amounts of the IRM compound of formula (I) and a PD-L1 inhibitor compound. In some embodiments, the method comprises treating a subject having a tumor by administering therapeutically effective amounts of the IRM compound of formula (I) and a PD-L2 inhibitor compound.

In some embodiments of the present disclosure, the method comprises administering the IRM compound of formula (I) and a blocking antibody of an immune checkpoint pathway. In some embodiments, the method comprises treating a subject having a tumor by administering therapeutically effective amounts of the IRM compound of formula (I) and an anti-CTLA-4 receptor antibody. In some embodiments, the method comprises treating a subject having a tumor by administering therapeutically effective amounts of the IRM compound of formula (I) and an anti-PD-1 receptor antibody.

In some embodiments, the method comprises treating a subject having a tumor by administering therapeutically effective amounts of the IRM compound of formula (I) and an anti-LAG-3 receptor antibody. In some embodiments, the method comprises treating a subject having a tumor by administering therapeutically effective amounts of the IRM compound of formula (I) and an anti-TIM-3 receptor antibody. In some embodiments, the method comprises treating a subject having a tumor by administering therapeutically effective amounts of the IRM compound of formula (I) and an anti-BTLA receptor antibody. In some embodiments, the method comprises treating a subject having a tumor by administering therapeutically effective amounts of the IRM compound of formula (I) and an anti-KIR receptor antibody. In some embodiments, the method comprises treating a subject having a tumor by administering therapeutically effective amounts of the IRM compound of formula (I) and an anti-PD-L1 antibody. In some embodiments, the method comprises treating a subject having a tumor by administering therapeutically effective amounts of the IRM compound of formula (I) and an anti-PD-L2 antibody.

In some embodiments of the present disclosure, the therapeutic combination comprises the IRM compound of formula (I) and a CTLA-4 receptor inhibitor compound. In some embodiments, the therapeutic combination comprises the IRM compound of formula (I) and a PD-1 receptor inhibitor compound. In some embodiments, the therapeutic combination comprises the IRM compound of formula (I) and a LAG-3 receptor inhibitor compound. In some embodiments, the therapeutic combination comprises the IRM compound of formula (I), a TIM-3 receptor inhibitor compound. In some embodiments, the therapeutic combination comprises the IRM compound of formula (I) and a BTLA receptor inhibitor compound. In some embodiments, the therapeutic combination comprises the IRM compound of formula (I) and a KIR receptor inhibitor compound. In some embodiments, the therapeutic combination comprises the IRM compound of formula (I) and a PD-L1 inhibitor compound. In some embodiments, the therapeutic combination comprises the IRM compound of formula (I) and a PD-L2 inhibitor compound.

In some embodiments of the present disclosure, the therapeutic combination comprises the IRM compound of formula (I) and a blocking antibody of an immune checkpoint pathway. In some embodiments, the therapeutic combination comprises the IRM compound of formula (I) and an anti-CTLA-4 receptor antibody. In some embodiments, the therapeutic combination comprises the IRM compound of formula (I) and an anti-PD-1 receptor antibody. In some embodiments, the therapeutic combination comprises the IRM compound of formula (I) and an anti-LAG-3 receptor antibody. In some embodiments, the therapeutic combination comprises the IRM compound of formula (I), an anti-TIM-3 receptor antibody. In some embodiments, the therapeutic combination comprises the IRM compound of formula (T) and an anti-BTLA receptor antibody. In some embodiments, the therapeutic combination comprises the IRM compound of formula (I) and an anti-KIR receptor antibody. In some embodiments, the therapeutic combination comprises the IRM compound of formula (I) and an anti-PD-L1 antibody. In some embodiments, the therapeutic combination comprises the IRM compound of formula (I) and an anti-PD-L2 antibody.

In some embodiments of the present disclosure, the anti-CTLA-4 receptor antibody is ipilimumab or tremelimumab. In some embodiments the anti-PD-1 receptor antibody is lambrolizumab, pidilizumab, or nivolumab. In some embodiments, the anti-KIR receptor antibody is lirilumab.

In some embodiments of the present disclosure, the method comprises treating a subject having a tumor by administering therapeutically effective amounts of the IRM compound of formula (I) and ipilimumab. In some embodiments, the method comprises treating a subject having a tumor by administering therapeutically effective amounts of the IRM compound of formula (I) and tremelimumab. In some embodiments, the method comprises treating a subject having a tumor by administering therapeutically effective amounts of the IRM compound of formula (I) and lambrolizumab. In some embodiments, the method comprises treating a subject having a tumor by administering therapeutically effective amounts of the IRM compound of formula (I) and pidilizumab. In some embodiments, the method comprises treating a subject having a tumor by administering therapeutically effective amounts of the IRM compound of formula (I) and nivolumab. In some embodiments, the method comprises treating a subject having a tumor by administering therapeutically effective amounts of the IRM compound of formula (I) and lirilumab.

In some embodiments of the present disclosure, the therapeutic combination comprises the IRM compound of formula (I) and ipilimumab. In some embodiments, the therapeutic combination comprises the IRM compound of formula (I) and tremelimumab. In some embodiments, the therapeutic combination comprises the IRM compound of formula (I) and lambrolizumab. In some embodiments, the therapeutic combination comprises the IRM compound of formula (I) and pidilizumab. In some embodiments, the therapeutic combination comprises the IRM compound of formula (I) and nivolumab. In some embodiments, the therapeutic combination comprises the IRM compound of formula (I) and lirilumab.

In some embodiments of the present disclosure, the method comprises administering the IRM compound of formula (I) and two different immune checkpoint inhibitor compounds. The two different immune inhibitor compounds can be selected from a CTLA-4 receptor inhibitor, a PD-1 receptor inhibitor, a LAG-3 receptor inhibitor, a TIM-3 receptor inhibitor, a BTLA receptor inhibitor, a KIR receptor inhibitor a PD-L1 inhibitor or a PD-L2 inhibitor. In some embodiments, the method comprises treating a subject having a tumor by administering therapeutically effective amounts of the IRM compound of formula (I), a CTLA-4 receptor inhibitor compound, and a PD-1 receptor inhibitor compound. In some embodiments, the method comprises treating a subject having a tumor by administering therapeutically effective amounts of the IRM compound of formula (I), a CTLA-4 receptor inhibitor compound, and a PD-L1 inhibitor compound. In some embodiments, the method comprises treating a subject having a tumor by administering therapeutically effective amounts of the IRM compound of formula (I), a PD-1 receptor inhibitor compound, and a LAG-3 receptor inhibitor compound. In some embodiments, the method comprises treating a subject having a tumor by administering therapeutically effective amounts the IRM compound of formula (I), a PD-1 receptor inhibitor compound, and a TIM-3 receptor inhibitor compound.

In some embodiments of the present disclosure, the method comprises treating a subject having a tumor by administering therapeutically effective amounts of the IRM compound of formula (I), an anti-CTLA-4 receptor antibody, and an anti-PD-L1 antibody. In some embodiments, the method comprises treating a subject having a tumor by administering therapeutically effective amounts of the IRM compound of formula (I), an anti-PD-1 receptor antibody, and an anti-LAG-3 receptor antibody. In some embodiments, the method comprises treating a subject having a tumor by administering therapeutically effective amounts of the IRM compound of formula (I), an anti-PD-1 receptor antibody, and an anti-TIM-3 receptor antibody. In some embodiments, the method comprises treating a subject having a tumor by administering therapeutically effective amounts of the IRM compound of formula (I), an anti-PD-1 receptor antibody, and either an anti-PD-L1 antibody or an anti-PD-L2 antibody. In some embodiments, the method comprises treating a subject having a tumor by administering therapeutically effective amounts of the IRM compound of formula (I), ipilimumab, and nivolumab. In some embodiments, the method comprises treating a subject having a tumor by administering therapeutically effective amounts of the IRM compound of formula (I), ipilimumab, and lambrolizumab.

In some embodiments, the therapeutic combination of the present disclosure comprises the IRM compound of formula (I) and two different immune checkpoint inhibitor compounds. The two different immune checkpoint inhibitor compounds can be selected from a CTLA-4 receptor inhibitor, a PD-1 receptor inhibitor, a LAG-3 receptor inhibitor, a TIM-3 receptor inhibitor, a BTLA receptor inhibitor, a KIR receptor inhibitor, a PD-L1 inhibitor, or a PD-L2 inhibitor.

In some embodiments, the therapeutic combination comprises the IRM compound of formula (I), a CTLA-4 receptor inhibitor compound, and a PD-1 receptor inhibitor compound. In some embodiments, the therapeutic combination comprises the IRM compound of formula (I), a CTLA-4 receptor inhibitor compound, and a PD-L1 inhibitor compound. In some embodiments, the therapeutic combination comprises the IRM compound of formula (I), a PD-1 receptor inhibitor compound, and a LAG-3 receptor inhibitor compound. In some embodiments, the therapeutic combination comprises the IRM compound of formula (I), a PD-1 receptor inhibitor compound, and a TIM-3 receptor inhibitor compound.

In some embodiments of the present disclosure, the therapeutic combination comprises the IRM compound of formula (I), an anti-CTLA-4 receptor antibody, and an anti-PD-L1 antibody. In some embodiments, the therapeutic combination comprises the IRM compound of formula (I), an anti-CTLA-4 antibody, and an anti-PD-1 antibody. In some embodiments, the therapeutic combination comprises the IRM compound of formula (I), an anti-PD-1 receptor antibody, and an anti-LAG-3 receptor antibody. In some embodiments, the therapeutic combination comprises the IRM compound of formula (I), an anti-PD-1 receptor antibody, and an anti-TIM-3 receptor antibody. In some embodiments, the therapeutic combination comprises the IRM compound of formula (I), an anti-PD-1 receptor antibody, and either an anti-PD-L1 antibody or an anti-PD-L2 antibody. In some embodiments, the therapeutic combination comprises the IRM compound of formula (I), ipilimumab, and nivolumab. In some embodiments, the therapeutic combination comprises the IRM compound of formula (I), ipilimumab, and lambrolizumab.

In some embodiments, the present disclosure provides a method for treating a solid tumor cancer. In some embodiments, the present disclosure provides a method for treating breast cancer, bladder cancer, head and neck cancer, non-small cell lung cancer, small cell lung cancer, colorectal cancer, gastrointestinal cancer, gastroesophageal cancer, renal cell cancer, prostate cancer, liver cancer, colon cancer, pancreatic cancer tumor, ovarian cancer tumor, lymphoma, cutaneous T-cell lymphoma, or melanoma.

In some embodiments, the present disclosure provides a method for treating a solid tumor. In some embodiments, the present disclosure provides a method for treating a breast cancer tumor, a bladder cancer tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, a cutaneous T-cell lymphoma, or a melanoma. In some embodiments, the present disclosure provides a method for treating an immune suppressed tumor. An immune suppressed tumor is a tumor that contains immune suppressive associated cells such as for example $T_{Reg}$ cells, myeloid derived suppressor cells (MDSC), M2 macrophages, and the like or immune suppressive factors such as inducible nitric oxide synthase (iNOS), PD-L1, and the like.

The precise amount of IRM compound of formula (I) incorporated in a particular method or therapeutic combination of the disclosure may vary according to factors known in art such as for example, the physical and clinical status of the subject, the method of administration, the content of the formulation, the intended dosing regimen or sequence. Accordingly, it is not practical to specifically set forth an amount that constitutes an amount of IRM compound therapeutically effective for all possible applications. Those of ordinary skill in the art, however, can readily determine an appropriate amount with due consideration of such factors.

In some embodiments of the present disclosure, the method includes administering an injectable formulation of IRM compound of formula (I) to a subject to provide a dose of IRM compound of formula (I) to the subject of from about 1 µg/kg to about 5 mg/kg based on the body mass of the subject.

The dose of the IRM compound of formula (I) or any immune checkpoint inhibitor compound may be calculated using actual body weight (or mass) of a subject obtained just prior to the beginning of the treatment course. In some embodiments, the dose may be calculated using body surface area of a subject. Body surface area ($m^2$) may be calculated prior to the beginning of the treatment course using the Dubois method: $m^2=(wt\ kg^{0.425} \times height\ cm^{0.725}) \times 0.007184$.

In some embodiments, the tumor size is based on the length of the longest dimension of the tumor to be injected. In some embodiments, the tumor to be injected comprises a longest dimension and wherein the longest dimension ranges from about 1.5 cm to about 5 cm.

Tumor dimensions and volumes can be determined using imaging procedures of the tumor such as three-dimensional ultrasound imaging, three-dimensional CT imaging, or three-dimensional MRI imaging.

Pharmaceutical formulations contemplated herein for an immune checkpoint inhibitor compound can be administered non-parenterally (through the digestive tract) or parenterally (administration other than through the digestive tract) with parenteral administration being a preferred embodiment.

Pharmaceutical formulations contemplated herein for administration of an immune checkpoint inhibitor compound include, but are not limited to, solution, suspension and emulsion formulations. Types of formulations include, but are not limited to aqueous formulations (e.g., phosphate or citrate buffered saline), oil formulations, polyol formulations (e.g., glycerol, polyethylene glycol), oil in water formulations, and water in oil formulations. Pharmaceutical formulations may further include one or more additives such as suspending agents, colorants, surfactants, tonicity agents, and dispersing agents.

In some embodiments of the present disclosure, the immune checkpoint inhibitor compound is incorporated in a pharmaceutically acceptable formulation. In some embodiments, the immune checkpoint inhibitor compound is incorporated in a pharmaceutically acceptable aqueous formulation. Examples of acceptable aqueous formulations include isotonic buffered and pH 4.5-8 adjusted saline solutions such as Lactated Ringer's Solution and the like.

In some embodiments of the present disclosure, the immune checkpoint inhibitor compound is incorporated in a pharmaceutically acceptable liposome formulation, wherein the formulation is a passive or targeted liposome formulation. Examples of methods for the preparation of suitable liposome formulations of antibodies are described U.S. Pat. No. 5,399,331 (Loughrey), U.S. Pat. No. 8,304,565 (Wu) and U.S. Pat. No. 7,780,882 (Chang).

In some embodiments of the present disclosure, the immune checkpoint inhibitor antibody is a dry, lyophilized solid that is reconstituted with an aqueous reconstitution solvent prior to use.

In some embodiments of the present disclosure, the immune checkpoint inhibitor antibody is incorporated in a pharmaceutically acceptable formulation and the pharmaceutically acceptable formulation is injected directly into a tumor. In some embodiments, the immune checkpoint inhibitor antibody is incorporated in a pharmaceutically acceptable formulation and the pharmaceutically acceptable formulation is injected into the peritumoral region surrounding a tumor. The peritumoral region may contain antitumor immune cells.

In some embodiments of the present disclosure, the immune checkpoint inhibitor antibody is incorporated in a pharmaceutically acceptable formulation and the pharmaceutically acceptable formulation is administered by intravenous injection or infusion. In some embodiments the immune checkpoint inhibitor antibody is incorporated in a pharmaceutically acceptable formulation and the pharmaceutically acceptable formulation is administered by subcutaneous injection or intradermal injection.

In some embodiments the immune checkpoint inhibitor antibody is incorporated in a pharmaceutically acceptable formulation and the pharmaceutically acceptable formulation is administered by intraperitoneal injection or lavage.

The precise amount of immune checkpoint inhibitor compound incorporated in a particular method or therapeutic combination of the disclosure may vary according to factors known in art such as for example, the physical and clinical status of the subject, the method of administration, the content of the formulation, the physical and chemical nature of the immune checkpoint inhibitor compound, the intended dosing regimen or sequence. Accordingly, it is not practical to specifically set forth an amount that constitutes an amount of IRM compound therapeutically effective for all possible applications. Those of ordinary skill in the art, however, can readily determine the appropriate amount with due consideration of such factors.

In some embodiments of the present disclosure, the method includes administering an injectable formulation of immune checkpoint inhibitor antibody to a subject to provide a dose of the immune checkpoint inhibitor antibody to the subject of from about 0.5 mg to about 25 mg per kg body mass of the subject. In some embodiments, the method includes administering an injectable formulation of an immune checkpoint inhibitor antibody to a subject to provide a dose of the immune checkpoint inhibitor antibody to the subject of from about 0.5 mg to about 15 mg per kg body mass of the subject. In some embodiments, the method includes administering an injectable formulation of an immune checkpoint inhibitor antibody to a subject to provide a dose of the immune checkpoint inhibitor antibody to the subject of from about 0.5 mg to about 10 mg per kg body mass of the subject.

When more than one immune checkpoint inhibitor compound is administered, the immune checkpoint inhibitor compounds can be administered in separate pharmaceutically acceptable formulations or combined together in the same formulation.

The IRM compound of formula (I) and the immune checkpoint inhibitor compound can both be administered on the same day or the doses can be spaced apart by several days or weeks. In some embodiments, the immune checkpoint inhibitor compound is administered within 1, 2, 3, 4, 5, 6, or 7 days of administration of the IRM compound of formula (I). In some embodiments, the immune checkpoint inhibitor compound is administered within 1-10 days of the IRM compound of formula (I) administration. In some embodiments, the immune checkpoint inhibitor compound is administered within 1-13 weeks, within 1-8 weeks, within 1-6 weeks, within 1-4 weeks, or within 1-2 weeks of administration of the IRM compound of formula (I). In some embodiments, the immune checkpoint inhibitor compound is administered within 4 months, within 3 months, within 2 months, or within 1 month of administration of the compound of formula (T). For the sake of clarity the term "within" includes time periods either before, after, or on the same day as administration of the IRM compound of formula (I). For example, administering within 1-2 weeks includes both 1-2 weeks before administration of the IRM compound of formula (I), 1-2 weeks after administration of the IRM compound of formula (I), as well as on the same day as administration of the IRM compound of formula (I).

A therapeutically effective amount is an amount that ameliorates at least one symptom or clinical sign of a tumor. Ameliorating at least one symptom or clinical sign of a tumor can include a decrease in the size of a tumor, stabilization in the size or growth of a tumor, a reduction in the rate of growth of a tumor, an increase in tumor necrosis, a change in the tumor structure such as disintegration, a change in a biochemical marker associated with decrease in tumor establishment, a decrease in tumor progression or a decrease in tumor survival.

An increase in at least one cell-mediated immune response of a cell population that includes cells of a tumor refers to an increase in at least one biochemical, histological, or immunological marker associated with improvement of the immunological profile of the tumor microenvironment. Markers in which an increase in the amount of the marker is associated with an improvement of the immunological profile of the tumor microenvironment include, but are not limited to, interferon-alpha; interferon-gamma; interferon inducible proteins; TNF-alpha; chemokines such as CCL2, CCL3, CCL4, CXCL2; activated T-cells; activated B-cells; activated NK-cells; tumor specific T-cells, activated tumor associated macrophages; chemokine receptors such as CCR6; or tumor associated lymphoid aggregates.

Markers associated with a tumor microenvironment can be determined, for example, by analysis of a biopsy (for example needle biopsy) from the tumor, the localized tumor region, or a tumor draining lymph node. Analysis for the markers can be done using standard techniques such as by histology (HNE stain), flow cytometry, gene expression assays (quantitative PCR), immunochemistry techniques, as well as other techniques commonly known to those of ordinary skill in the art.

Direct injection of the compound of formula (I) or an immune checkpoint inhibitor compound into a tumor involves injection of the formulation directly into the interior of a tumor mass. Typically an 18 to 26 gauge syringe needle is used and in order to more precisely deliver the formulation, the insertion of the needle can be accomplished using medical imaging techniques such as ultrasound for delivery guidance. In some embodiments, the syringe needle is inserted in a tumor mass so that the entire fluid channel opening located at the tip of the syringe needle is positioned in the interior of the tumor mass. Once the needle tip is in the desired position in the tumor mass, the formulation can be injected into the tumor.

The present disclosure provides for therapeutic combinations that include the IRM compound of formula (I) and an immune checkpoint inhibitor compound. Therapeutic combinations of the present invention also include combinations of the IRM compound of formula (I) and one or more immune checkpoint inhibitor compounds. A therapeutic combination may be part of a single pharmaceutical formulation in which the IRM compound of formula (I) and the immune checkpoint inhibitor compound are administered together in the single formulation. In a preferred embodiment of the present disclosure, the therapeutic composition the IRM compound of formula (I) and the immune checkpoint inhibitor compound are incorporated in separate pharmaceutical formulations and as such are administered separately such as, for example, at different times, and by different routes of administration.

In some embodiments of the present disclosure, both the formulation of the IRM compound (I) and the formulation of an immune checkpoint inhibitor compound are injected into the same tumor or into the area immediately surrounding the outer edge of that tumor.

Unless otherwise indicated, reference to a compound can include the compound in any pharmaceutically acceptable form, including any isomer (e.g., diasteriomer or enantiomer), salt, solvate, polymorph, and the like. In particular, if a compound is optically active, reference to the compound can include each of the enantiomers, as well as racemic mixtures of the enantiomers.

The pharmaceutical formulations of the disclosure may further include one or more additives including, but not limited to, antioxidants, antimicrobials, adjuvants, thickeners, suspending agents, surfactants, and dispersing agents. In some embodiments the formulation can include an added antioxidant such as butylated hydroxyanisole (BHA) or butylatedhydroxytoluene (BHT). The added antioxidant concentration in the formulation can be at least 10 ppm, 50 ppm, 100 ppm, 200 ppm, and up to 300 ppm.

The TLR agonism for a particular compound may be assessed in any suitable manner. For example, suitable assays for detecting TLR agonism are described in U.S. Patent Publication No. US2004/0132079, and recombinant cell lines suitable for use in such assays are described, for example, in International Patent Publication No. WO 04/053057.

The present disclosure also provides for a kit for treating a tumor. The kit can comprise at least one checkpoint inhibitor compound; N-(4-{[4-amino-2-butyl-1H-imidazo[4,5-c]quinolin-1-yl]oxy}butyl)octadecanamide, or a pharmaceutically acceptable salt thereof; and a set of instructions for use.

In some embodiments of the kit, the N-(4-{[4-amino-2-butyl-1H-imidazo[4,5-c]quinolin-1-yl]oxy}butyl)octadecanamide, or a pharmaceutically acceptable salt thereof is stored in a separate container from the at least one immune checkpoint inhibitor compound.

In some embodiments of the kit, the at least one immune checkpoint inhibitor compound is a CTLA-4 receptor inhibitor, PD-1 receptor inhibitor, PD-L1 inhibitor, or PD-L2 inhibitor, a LAG-3 receptor inhibitor, a TIM-3 receptor inhibitor, a BTLA receptor inhibitor, a KIR receptor inhibitor, or a combination of any of the foregoing immune checkpoint inhibitor compounds.

In some embodiments of the kit, the immune checkpoint inhibitor compound is an antibody or an antibody fragment.

In some embodiments of the kit, the at least one immune checkpoint inhibitor compound is an anti-CTLA-4 receptor antibody, an anti-PD-1 receptor antibody, an anti-LAG-3 receptor antibody, an anti-TIM-3 receptor antibody, an anti-BTLA receptor antibody, an anti-KIR receptor antibody, an anti-PD-L1 antibody, or an anti-PD-L2 antibody, or a combination of any of the foregoing antibodies.

In some embodiments of the kit, the at least one immune checkpoint inhibitor compound is in the form of a lyophilized solid.

In some embodiments, the kit, further comprises an aqueous reconstitution solvent.

In some embodiments of the kit, the at least one immune checkpoint inhibitor compound is incorporated in a first pharmaceutically acceptable formulation and the N-(4-{[4-amino-2-butyl-1H-imidazo[4,5-c]quinolin-1-yl]oxy}butyl)octadecanamide is incorporated in a second pharmaceutically acceptable formulation.

In some embodiments of the kit, the N-(4-{[4-amino-2-butyl-1H-imidazo[4,5-c]quinolin-1-yl]oxy}butyl)octadecanamide is incorporated in a formulation comprising sesame oil and ethanol Certain embodiments of the methods, combinations, and kits of the present disclosure are set forth in the following list of embodiments.

EMBODIMENTS

Embodiment 1 is a method for treating a subject having a tumor, comprising administering a therapeutically effective amount of a first immune checkpoint inhibitor compound to the subject; and administering a therapeutically effective amount of an IRM compound to the subject; wherein the IRM compound is N-(4-{[4-amino-2-butyl-1H-imidazo[4,5-c]quinolin-1-yl]oxy}butyl)octadecanamide, or a pharmaceutically acceptable salt thereof.

Embodiment 2 is a therapeutic combination for treating a tumor comprising: a therapeutically effective amount of a first immune checkpoint inhibitor compound; and a therapeutically effective amount of an IRM compound, wherein the IRM compound is N-(4-{[4-amino-2-butyl-1H-imidazo[4,5-c]quinolin-1-yl]oxy}butyl)octadecanamide, or a pharmaceutically acceptable salt thereof.

Embodiment 3 is the method of embodiment 1 or the therapeutic combination of embodiment 2, wherein the first immune checkpoint inhibitor compound is incorporated in a first pharmaceutically acceptable formulation.

Embodiment 4 is the method or therapeutic combination of embodiment 3, wherein the first pharmaceutically acceptable formulation is an aqueous formulation.

Embodiment 5 is the method embodiment 3 or 4, wherein the first pharmaceutically acceptable formulation is injected directly into a tumor.

Embodiment 6 is the method of embodiment 3 or 4, wherein the first pharmaceutically acceptable formulation is administered by intravenous infusion.

Embodiment 7 is the method of any of the embodiments 1 and 3-6 or the therapeutic combination of any of the embodiments 2-4, wherein the IRM compound is incorporated in a second pharmaceutically acceptable formulation.

Embodiment 8 is the method or therapeutic combination of embodiment 7, wherein the second pharmaceutically acceptable formulation comprises sesame oil and ethanol.

Embodiment 9 is the method or therapeutic combination of embodiment 8, wherein the ethanol is present in the second pharmaceutically acceptable formulation in an amount of from 1 wt-% to 9 wt-%.

Embodiment 10 is the method or therapeutic combination of embodiment 9, wherein the ethanol is present in the second pharmaceutically acceptable formulation in an amount from 7 wt-% to 8 wt-%.

Embodiment 11 is the method of embodiment 7 or the therapeutic combination of embodiment 7, wherein the IRM compound is incorporated into a liposome formulation.

Embodiment 12 is the method or therapeutic combination of any of the embodiments 7-11, wherein the second pharmaceutically acceptable formulation is injected directly into a tumor.

Embodiment 13 is the method of any one of the embodiments 1 and 3-12 or the therapeutic combination of any of the embodiments 2-4 and 7-11, wherein the immune checkpoint inhibitor compound is a CTLA-4 receptor inhibitor, PD-1 receptor inhibitor, PD-L1 inhibitor, PD-L2 inhibitor, a LAG-3 receptor inhibitor, a TIM-3 receptor inhibitor, a BTLA receptor inhibitor, or a KIR receptor inhibitor.

Embodiment 14 is the method of any one of the embodiments 1 and 3-13 or the therapeutic combination of any of the embodiments 2-4, 7-11, and 13, wherein the immune checkpoint inhibitor compound is an antibody or antibody fragment.

Embodiment 15 is the method or therapeutic combination of embodiment 14, wherein the immune checkpoint inhibitor compound is an anti-CTLA-4 receptor antibody, an anti-PD-1 receptor antibody, an anti-PD-L1 antibody, or an anti-PD-L2 antibody.

Embodiment 16 is the method of any of the embodiments 1 and 3-15, wherein the tumor is a breast cancer tumor, a bladder cancer tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, or a cutaneous T-cell lymphoma, or a melanoma.

Embodiment 17 is the method of any of the embodiments 3-16 or the therapeutic combination of any of the embodiments 3-4, 7-11, and 13 further comprising a second immune checkpoint inhibitor compound.

Embodiment 18 is the method or therapeutic combination of embodiment 17, wherein the second immune checkpoint inhibitor compound is incorporated in a third pharmaceutically acceptable formulation.

Embodiment 19 is the method or therapeutic combination of embodiment 18, wherein the third pharmaceutically acceptable formulation is an aqueous formulation.

Embodiment 20 is the method of embodiment 18, wherein the third pharmaceutically acceptable formulation is injected directly into a tumor.

Embodiment 21 is the method of embodiment 18, wherein the third pharmaceutically acceptable formulation is administered by intravenous infusion.

Embodiment 22 is the method or therapeutic combination of embodiment 17, wherein the first and second immune checkpoint inhibitors are both incorporated in the first pharmaceutically acceptable formulation.

Embodiment 23 is a kit for treating a tumor comprising at least one immune checkpoint inhibitor compound; an IRM compound;
wherein the IRM compound is N-(4-{[4-amino-2-butyl-1H-imidazo[4,5-c]quinolin-1-yl]oxy}butyl)octadecanamide, or a pharmaceutically acceptable salt thereof;
and a set of instructions for use.

Embodiment 24 is the kit of embodiment 23, wherein the at least one immune checkpoint inhibitor compound is a CTLA-4 receptor inhibitor, PD-1 receptor inhibitor, PD-L1 inhibitor, or PD-L2 inhibitor, a LAG-3 receptor inhibitor, a TIM-3 receptor inhibitor, a BTLA receptor inhibitor, a KIR receptor inhibitor, or a combination of any of the foregoing immune checkpoint inhibitor compounds.

Embodiment 25 is the kit of embodiment 23, wherein the immune checkpoint inhibitor compound is an antibody or an antibody fragment.

Embodiment 26 is the kit of embodiment 24, wherein the at least immune checkpoint inhibitor compound is an anti-CTLA-4 receptor antibody, an anti-PD-1 receptor antibody, an anti-PD-L1 antibody, an anti-PD-L2 antibody, or a combination of any of the foregoing antibodies.

Embodiment 27 is the kit of any of the embodiments 22-25, wherein the at least one immune checkpoint inhibitor compound is in the form of a lyophilized solid.

Embodiment 28 is the kit of any of the embodiments 22-26 further comprising an aqueous reconstitution solvent.

Embodiment 29 is the kit of any of the embodiments 22-27, wherein the at least one immune checkpoint inhibitor compound is incorporated in a first pharmaceutically acceptable formulation and the N-(4-{[4-amino-2-butyl-1H-imidazo[4,5-c]quinolin-1-yl]oxy}butyl)octadecanamide is incorporated in a second pharmaceutically acceptable formulation.

Embodiment 30 is the kit of any of the embodiments 22-28, wherein the N-(4-{[4-amino-2-butyl-1H-imidazo[4,5-c]quinolin-1-yl]oxy}butyl)octadecanamide is incorporated in a formulation comprising sesame oil and ethanol.

Objects and advantages of this disclosure are further illustrated by the following examples, but the particular materials and amounts thereof recited in these examples, as well as other conditions and details, should not be construed to unduly limit the disclosure of this invention.

The complete disclosures of the patents, patent documents, and publications cited herein are incorporated by reference in their entirety as if each were individually incorporated. In the event that any inconsistency exists between the disclosure of the present application and the disclosure(s) of any document incorporated herein by reference, the disclosure of the present application shall govern. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

EXAMPLES

Materials

C57BL/6 mice were obtained from the National Cancer Institute of the United States Department of Health and Human Services (Bethesda, Md.). All mice were 6-12 weeks of age.

The B16.F10 melanoma cell line was cultured in RPMI-1640 that was supplemented with 10% heat inactivated FBS, L-glutamine, sodium pyruvate, non-essential amino acids, and penicillin-streptomycin.

Mouse specific antibodies against PD-L1 (10F.9G20), CTLA-4 (9H10) and the respective isotype controls, Rat IgG2b (LTF-2) and Hamster IgG (BE0091), were obtained from Bio-X-Cell (West Lebanon, N.H.). All antibodies were formulated in PBS at pH 7.

N-(4-{[4-amino-2-butyl-1H-imidazo[4,5-c]quinolin-1-yl]oxy}butyl)octadecanamide was prepared as described in U.S. Patent Application No. 2013/0230578 and formulated as a solution in sesame oil/5 wt-% ethanol. The formulation was filtered through a polyethersulfone 0.2 μM filter (Millipore, Billerica, Mass.). The drug content in the formulations used was 0.5 mg/mL as determined by HPLC. A filtered sesame oil/5 wt-% ethanol formulation without N-(4-{[4-amino-2-utyl-1H-imidazo[4,5-c]quinolin-1-yl]

oxy}butyl)octadecanamide as a component served as the vehicle control for Examples 1-3.

Statistics

All results are expressed as the mean+/−SEM. Group sizes were n=5, unless otherwise indicated. Statistical analysis was performed with GraphPad Prism 4 software (GraphPad Software Inc., La Jolla, Calif.). Data were analyzed using unpaired two tailed t tests, and differences were considered significant at p less than 0.05. FIGS. 1-5 denote statistical significance of p less than 0.05 as "*", p less than 0.005 as "", and p less than 0.005 as "*". Survival experiments utilized log rank Mantel-Cox test for survival analysis.

Example 1

The melanoma cell line B16.F10 was injected subcutaneously in the left flank of C57BL/6 mice. Each mouse was injected with 3×10' cells. Seven days post tumor implantation, the tumors were observable by external examination and the tumor size for each mouse was determined using an external digital caliper. Tumor size ($mm^2$) was expressed as the product of perpendicular diameter caliper measurements. The mice were then randomized into four treatment groups of five mice per group (Groups A-D).

Figure 2:
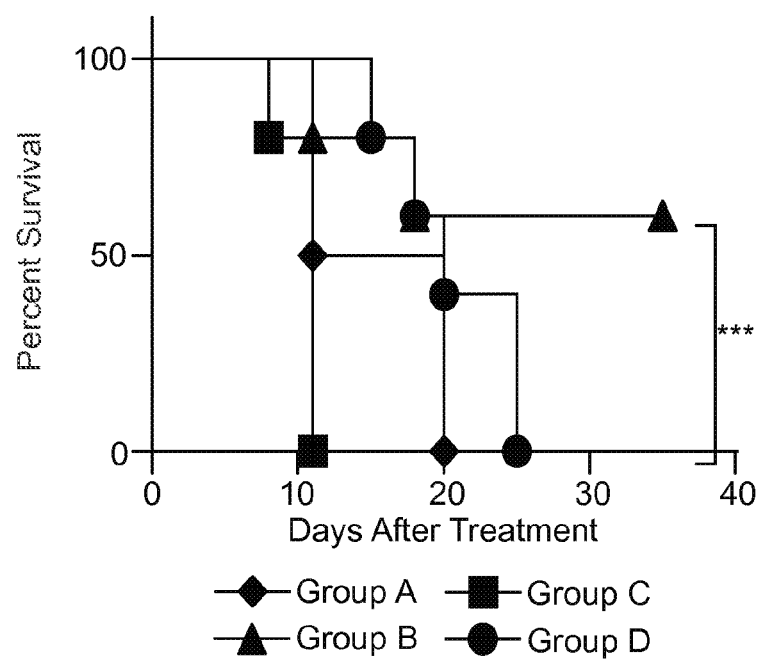
FIG. 2 is a chart of percent survival over time and compares treatment with a therapeutic combination of the compound of formula (I)+anti-CTLA-4 antibody (Group B) to monotherapy and vehicle control groups (Groups A, C, and D).

Beginning on day seven post tumor implantation, the mice in each group were dosed with separate regimens. Mice in Group A received a 70 µL injection of the sesame oil/ethanol vehicle control and a 200 µg intraperitoneal injection of anti-CTLA-4 antibody; both were dosed on day seven and day eleven with repeated 200 µg intraperitoneal injections of anti-CTLA-4 antibody administered every 4 days thereafter. Mice in Group B received an intratumoral injection of N-(4-{[4-amino-2-butyl-1H-imidazo[4,5-c]quinolin-1-yl]oxy}butyl)octadecanamide (35 µg) and a 200 µg intraperitoneal injection of anti-CTLA-4 antibody both dosed on day seven and day eleven with repeated 200 µg intraperitoneal injections of anti-CTLA-4 antibody administered every 4 days thereafter. Mice in Group C served as a control group and received a 70 µL injection of the sesame oil/ethanol vehicle control and a 200 µg intraperitoneal injection of isotype control IgG; both were dosed on day seven and day eleven with repeated 200 µg intraperitoneal injections of IgG administered every 4 days thereafter. Mice in Group D received an intratumoral injection of N-(4-{[4-amino-2-butyl-1H-imidazo[4,5-c]quinolin-1-yl]oxy}butyl)octadecanamide (35 µg) and a 200 µg intraperitoneal injection of isotype control IgG; both were dosed on day seven and day eleven with repeated 200 µg intraperitoneal injections of IgG administered every 4 days thereafter. The mice were observed during the treatment period and tumor size at the implantation site was measured at regular intervals for each mouse. Live mice with tumor size measured at the implantation site of less than 200 $mm^2$ and having no evidence of a skin ulceration were continued in the study until the next measurement timepoint. Mice with either tumor measured at the implantation site of greater than 200 $mm^2$ or having evidence of a skin ulceration were sacrificed on the tumor measurement date and recorded as non-survivors. Survival data at each time point was determined as the number of live mice with tumors at the implantation site of less than 200 $mm^2$. In FIG. 1 the mean tumor size (+/−SEM) at the implantation site for each Group is graphed versus time (days post initiation of dosing). In FIG. 2, the percent of mice surviving in each group is graphed versus time (days post initiation of dosing).

Example 2

The melanoma cell line B16.F10 was injected subcutaneously in the left flank of C57BL/6 mice. Each mouse was injected with 3×10⁵ cells. Seven days post tumor implantation, the tumors were observable by external examination and the tumor size for each mouse was determined using an external digital caliper. Tumor size ($mm^2$) was expressed as the product of perpendicular diameter caliper measurements. The mice were then randomized into four treatment groups of five mice per group (Groups E-H).

Figure 3:
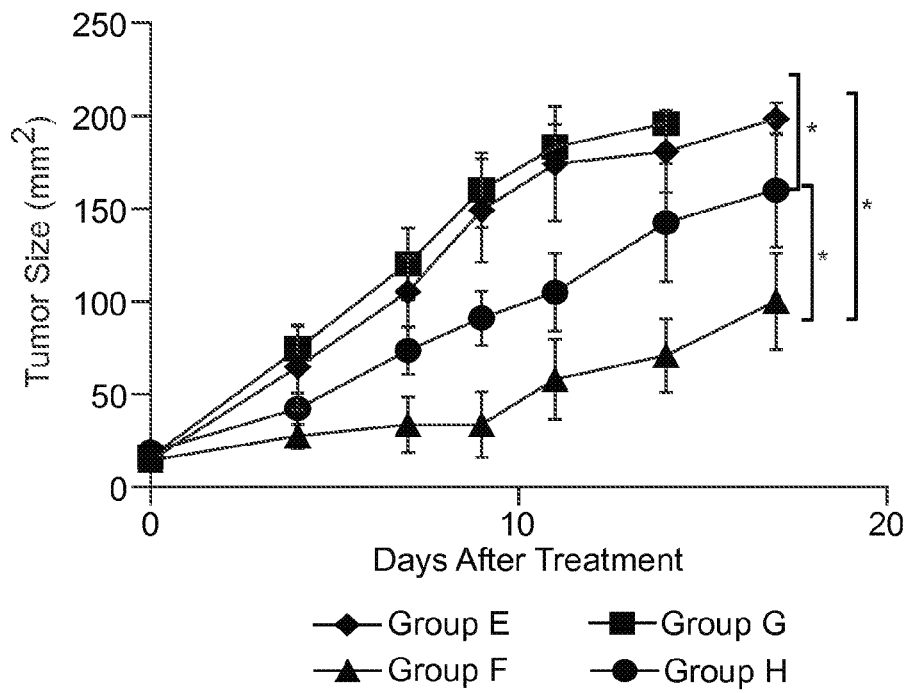
FIG. 3 is a chart of the growth in tumor size over time and compares treatment with a therapeutic combination of the compound of formula (I)+anti-PD-L1 antibody (Group F) to monotherapy and vehicle control groups (Groups E, G, and H).
Figure 4:
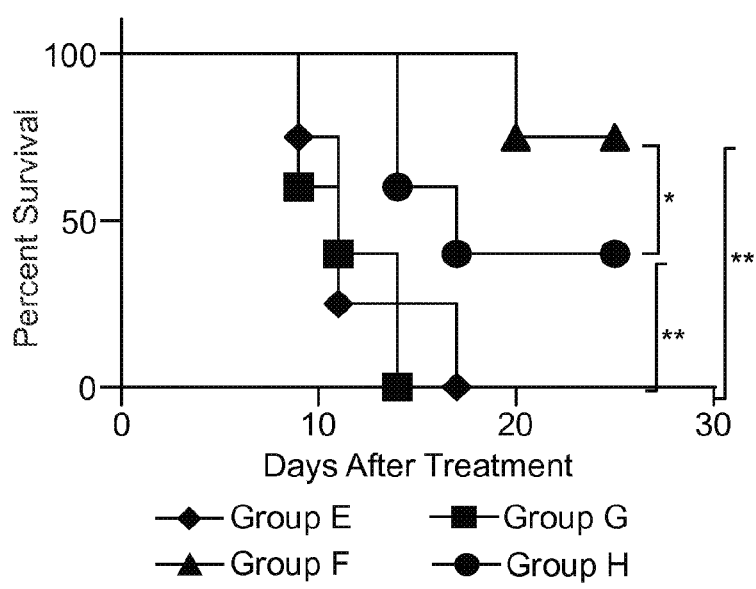
FIG. 4 is a chart of percent survival over time and compares treatment with a therapeutic combination of the compound of formula (I)+anti-PD-L1 antibody (Group F) to monotherapy and vehicle control groups (Groups E, G, and H).

Beginning on day seven post tumor implantation, the mice in each group were dosed with separate regimens. Mice in Group E received a 70 µL injection of the sesame oil/ethanol vehicle control and a 200 µg intraperitoneal injection of anti-PD-L1 antibody both were dosed on day seven and day eleven with repeated 200 µg intraperitoneal injections of anti-PD-L1 antibody administered every 4 days thereafter. Mice in Group F received an intratumoral injection of N-(4-{[4-amino-2-butyl-1H-imidazo[4,5-c]quinolin-1-yl]oxy}butyl)octadecanamide (35 µg) and a 200 µg intraperitoneal injection of anti-PD-L1 antibody; both were dosed on day seven and day eleven with repeated 200 µg intraperitoneal injections of anti-PD-L1 antibody administered every 4 days thereafter. Mice in Group G served as a control group and received a 70 µL injection of the sesame oil/ethanol vehicle control and a 200 µg intraperitoneal injection of isotype control IgG both were dosed on day seven and day eleven with repeated 200 µg intraperitoneal injections of IgG administered every 4 days thereafter. Mice in Group H received an intratumoral injection of N-(4-{[4-amino-2-butyl-1H-imidazo[4,5-c]quinolin-1-yl]oxy}butyl)octadecanamide (35 µg) and a 200 µg intraperitoneal injection of isotype control IgG; both were dosed on day seven and day eleven with repeated 200 µg intraperitoneal injections of IgG administered every 4 days thereafter. The mice were observed during the treatment period and tumor size at the implantation site was measured at regular intervals for each mouse. Live mice with tumor size measured at the implantation site of less than 200 $mm^2$ and having no evidence of a skin ulceration were continued in the study until the next measurement timepoint. Mice with tumor measured at the implantation site of greater than or equal to 200 $mm^2$ or having evidence of a skin ulceration were sacrificed on the tumor measurement date and recorded as non-survivors. Survival data at each time point was determined as the number of live mice with tumors at the implantation site of less than 200 $mm^2$. In FIG. 3 the mean tumor size (+/−SEM) at the implantation site for each Group is graphed versus time (days post initiation of dosing). In FIG. 4, the percent of mice surviving in each group is graphed versus time (days post initiation of dosing).

Example 3

The melanoma cell line B16.F10 was injected subcutaneously in the left and right flanks of C57BL/6 mice. Each mouse was initially injected in the left flank with 3×10⁵ cells. Four days after initial injection of cells in the left flank, each mouse was injected in the right flank with 3×10⁵ cells. Seven days post tumor implantation, the tumors were observable by external examination and the tumor size for each mouse was determined using an external digital caliper. Tumor size ($mm^2$) was expressed as the product of perpendicular diameter caliper measurements. The mice were then randomized into four treatment groups of five mice per group (Groups I-L).

Figure 5:
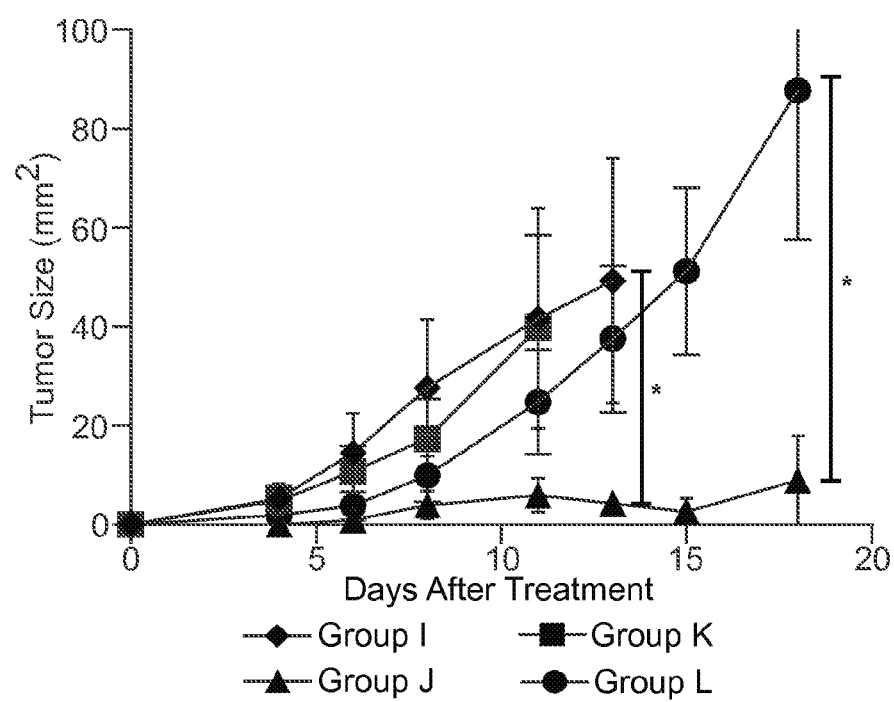
FIG. 5 is a chart of the growth in tumor size over time and compares treatment with a therapeutic combination of the compound of formula (T)+anti-CTLA-4 antibody+anti-PD-L1 antibody (Group J) to monotherapy and vehicle control groups (Groups I, K, and L).

Beginning on day seven post tumor implantation, the mice in each group were dosed with separate regimens. All Mice in Group I received a 70 µL injection of the sesame oil/ethanol vehicle control (injected in the left flank tumor mass), a 100 µg intraperitoneal injection of anti-PD-L1 antibody, and a 100 µg intraperitoneal injection of anti-CTLA-4 antibody with all three components dosed on both day seven and day eleven. In addition, all of the mice in Group I were administered a 100 µg intraperitoneal injection of anti-PD-L1 antibody and a 100 µg intraperitoneal injection of anti-CTLA-4 antibody every 4 days thereafter. Mice in Group J received an intratumoral injection of N-(4-{[4-amino-2-butyl-1H-imidazo[4,5-c]quinolin-1-yl]oxy}butyl) octadecanamide (35 µg) (injected in the left flank tumor mass), a 100 µg intraperitoneal injection of anti-PD-L1 antibody, a 100 µg intraperitoneal injection of anti-CTLA-4 antibody with all three components dosed on day seven and day eleven. In addition, all of the mice in Group J were administered a 100 µg intraperitoneal injection of anti-PD-L1 antibody and a 100 µg intraperitoneal injection of anti-CTLA-4 antibody every 4 days thereafter. Mice in Group K served as a control group and received a 70 µL injection of the sesame oil/ethanol vehicle control (injected in the left flank tumor mass) and a 200 µs intraperitoneal injection of isotype control IgG; both were dosed on day seven and day eleven with repeated 200 µg intraperitoneal injections of IgG administered every 4 days thereafter. Mice in Group L received an intratumoral injection of N-(4-{[4-amino-2-butyl-1H-imidazo[4,5-c]quinolin-1-yl]oxy}butyl)octadecanamide (35 µg) (injected in the left flank tumor mass) and a 200 µg intraperitoneal injection of isotype control IgG; both were dosed on day seven and day eleven with repeated 200 µg intraperitoneal injections of IgG administered every 4 days thereafter. For the sake of clarity, in all groups only the left flank tumor mass was injected with N-(4-{[4-amino-2-butyl-1H-imidazo[4,5-c]quinolin-1-yl]oxy}butyl)octadecanamide or sesame oil/ethanol vehicle (i.e., the right flank tumor mass was never injected with IRM or vehicle). The mice were observed during the treatment period and tumor size at the implantation site was measured at regular intervals for each mouse. Live mice with tumor size measured at the implantation site of less than 200 mm$^2$ and having no evidence of a skin ulceration were continued in the study until the next measurement timepoint. Mice with a tumor measured at one of the implantation sites of greater than or equal to 200 mm$^2$ or having evidence of a skin ulceration were sacrificed on the tumor measurement date and recorded as non-survivors. Survival data at each time point was determined as the number of live mice with tumors at the implantation site of less than 200 mm$^2$. In FIG. 5 the mean tumor size (+/−SEM) of the tumor mass on the right flank (i.e., the tumor mass opposite from the injection site) is graphed versus time (days post initiation of dosing). A statistically significant reduction in tumor growth is observed for Group J compared to the other groups.

What is claimed is:

1. A method of treating a tumor in a subject in need thereof, comprising administering a therapeutically effective amount of a PD-L1 antibody to the subject; and administering a therapeutically effective amount of an IRM compound to the subject; wherein the IRM compound is N-(4-{[4-amino-2-butyl-1H-imidazo[4,5-c]quinolin-1-yl]oxy}butyl)octadecanamide, or a pharmaceutically acceptable salt thereof.

2. A method of treating a tumor in a subject in need thereof, comprising administering a therapeutically effective amount of a CTLA-4 antibody to the subject; and administering a therapeutically effective amount of an IRM compound to the subject; wherein the IRM compound is N-(4-{[4-amino-2-butyl-1H-imidazo[4,5-c]quinolin-1-yl]oxy}butyl)octadecanamide, or a pharmaceutically acceptable salt thereof.

3. A method of treating a tumor in a subject in need thereof, comprising administering a therapeutically effective amount of a PD-L1 antibody to the subject; and administering a therapeutically effective amount of a CTLA-4 antibody to the subject; and administering a therapeutically effective amount of an IRM compound to the subject; wherein the IRM compound is N-(4-{[4-amino-2-butyl-1H-imidazo[4,5-c]quinolin-1-yl]oxy}butyl)octadecanamide, or a pharmaceutically acceptable salt thereof.

4. The method of any one of claims 1-3, wherein N-(4-{[4-amino-2-butyl-1H-imidazo[4,5-c]quinolin-1-yl]oxy}butyl)octadecanamide is injected directly into the tumor.

5. The method of claim 4, wherein the tumor is a breast cancer tumor, a bladder cancer tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, or a cutaneous T-cell lymphoma, or a melanoma.

* * * * *